United States Patent [19]

Hoffer

[11] Patent Number: 4,662,882
[45] Date of Patent: May 5, 1987

[54] INTRAOCULAR LENS

[76] Inventor: Kenneth J. Hoffer, 1407 Georgina Ave., Santa Monica, Calif. 90402

[21] Appl. No.: 800,201

[22] Filed: Nov. 21, 1985

[51] Int. Cl.⁴ .............................................. A61F 2/16
[52] U.S. Cl. ........................................................ 623/6
[58] Field of Search ............................................ 623/6

[56] References Cited

U.S. PATENT DOCUMENTS 4,485,499  12/1984  Castleman ............................... 623/6
4,575,877  3/1986  Herrick .................................... 623/6

Primary Examiner—Ronald L. Frinks
Attorney, Agent, or Firm—Pretty, Schroeder, Brueggemann & Clark

[57] ABSTRACT

An intraocular lens is provided for implantation in a human eye, preferably after extracapsular cataract extraction, having a lens body and resilient lens centering strands. The strands extend from the lens body and curve behind and underneath a rear surface of the lens body before curving radially outwardly for engaging eye tissue. The portion of the strands curving behind and underneath that rear surface contacts the posterior capsule of the eye and creates a space between the lens body and posterior capsule which prevents damage to the lens body when performing a laser discission of the posterior capsule.

16 Claims, 6 Drawing Figures

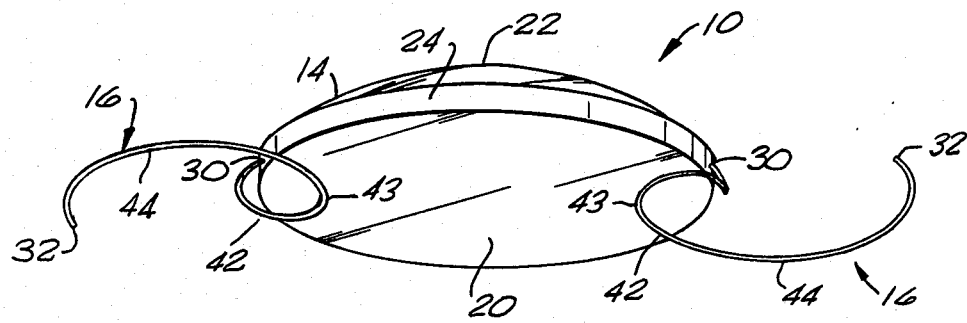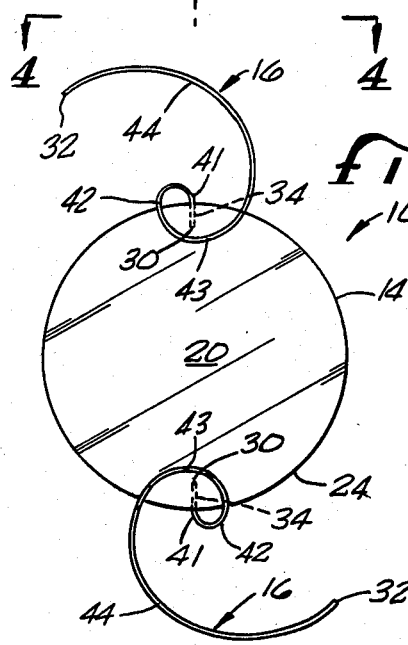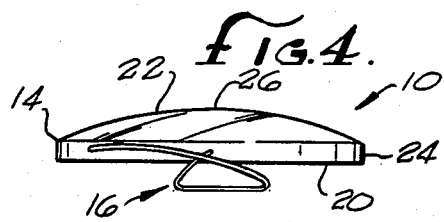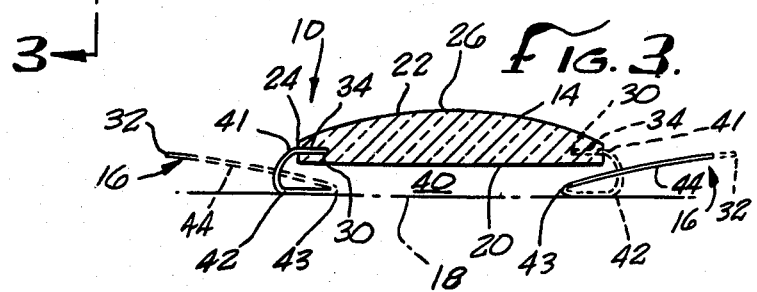

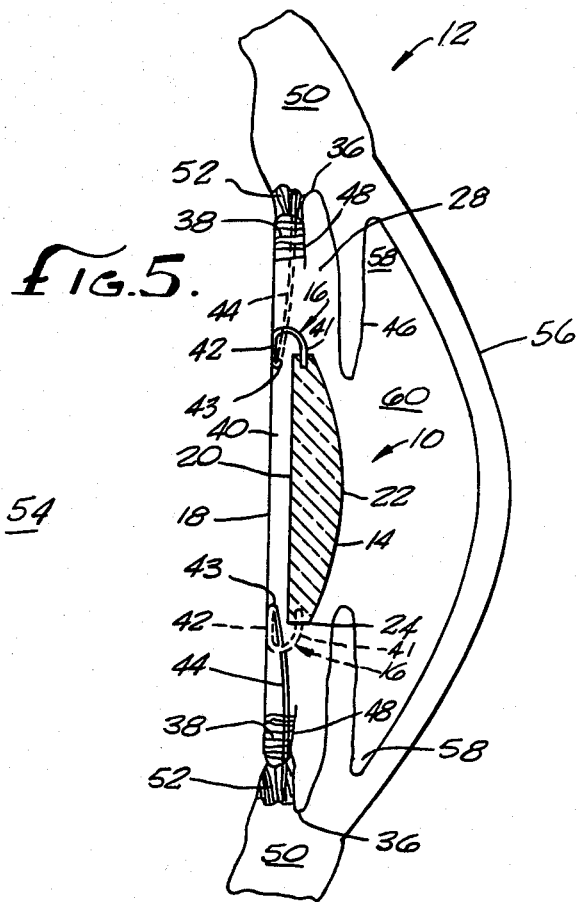
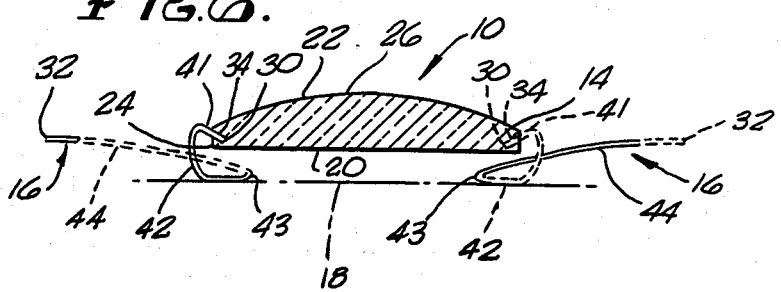

INTRAOCULAR LENS

BACKGROUND OF THE INVENTION

The present invention relates generally to intraocular lenses and, more particularly, to a posterior chamber lens for implantation following extracapsular cataract extraction.

For various reasons, the natural lens of a human eye can sometimes become clouded and obstruct the passage of light. This clouding of the lens is known as a cataract and generally worsens with the passage of time. Often times, the cataract becomes so severe that the passage of light through the lens is completely blocked, and the person afflicted with this condition eventually is unable to see. In such instances, it is usually necessary to surgically remove the cataract and replace the natural lens with an artificial intraocular lens to restore vision.

To remove the cataract, a form of surgery known as extracapsular cataract extraction commonly is used. This surgery involves making an incision in the front wall of the eye into the anterior chamber. The pupil is dilated to give access to the posterior chamber where the natural lens is situated. The surgeon then opens the anterior capsule or front wall of the natural human lens and removes the clouded lens nucleus by various known techniques, such as expression or phacoemulsification. The transparent posterior capsule or rear wall of the lens is left intact and, depending upon one's surgical techniques, some peripheral portions of the anterior capsule known as the annular capsular flaps also are left intact. An intraocular lens may then be implanted in the posterior chamber to replace the natural lens and restore vision.

Extracapsular surgery generally has been preferred over other surgical techniques for cataract removal primarily because the intact posterior capsule serves several beneficial functions. For example, the posterior capsule acts as a barrier to the migration of vitreous humor from its normal position behind the lens. The posterior capsule also reduces the chance of developing a condition known as cystoid macula edema, which is a swelling of the macula of the retina. This condition occurs when certain enzymes are released from the iris and migrate through the vitreous humor back to the macula to cause undesirable swelling. Leaving the posterior capsule intact substantially prevents these problems.

While the extracapsular form of surgery has many advantages, there are some problems associated with it. For example, after the clouded lens material is removed, the surgeon typically will scrape or "polish" the posterior capsule to remove as much of the lens material as possible. However, it is virtually impossible to completely remove all the living lens cells from the capsule, and, as time goes by, the remaining cells continue to reproduce and grow, forming a glistening, bubbly, vision-impairing material known as Elschnig's pearls. Another vision-impairing phenemenon, known as fibrosis, occurs when remnant lens fibers on the posterior capsule create opacities which block the passage of light to the retina and cause partial or complete opacification of the capsule. Other potential problems include pigmentary or inflamatory deposits on the posterior capsule, and wrinkling or corrugating of the capsule.

When vision impairment from Elschnig's pearls, fibrosis or other causes is present, it is usually necessary to perform a surgical procedure to open or remove part of the clouded posterior capsule to restore proper vision. The surgical procedure is commonly referred to as a discission or secondary capsulotomy. For many years, discissions have been performed with a laser, such as a neodymium-YAG laser. Laser discissions are now widely used and accepted, primarily because they are relatively safe and effective, and, importantly, they do not require an invasive surgical procedure to open the capsule. The former technique of opening or removing part of the clouded posterior capsule, which has been substantially displaced by the laser technique, involves making an incision in the eye and inserting a needle or other mechanical instrument to tear open the clouded capsule. The primary advantages of the non-invasive nature of the laser discission are that the risks of infection and other complications are reduced, and the procedure can be performed in a few minutes in a doctor's office, instead of in a hospital operating room.

In performing a laser discission, the laser beam is focused on the clouded posterior capsule and the beam is pulsed to sufficiently open the clouded capsule. One of the problems associated with laser discissions is the possible damage to the implanted lens. After implantation, the rear surface of the intraocular lens usually is in intimate contact with the posterior capsule. When the laser beam is focused and pulsed, an explosion occurs at the focused area creating a "sphere of explosion." If the sphere of explosion encompasses the intraocular lens, the lens can sustain damage in the form of vision-impairing pits or cracks. This undesirable lens damage can occur even when the laser beam is properly focused, due to the intimate contact between the lens and posterior capsule. It is therefore advantageous to provide a spacing between the capsule and the implanted lens to position the rear surface of the lens outside the laser beam's sphere of explosion.

Several intraocular lenses have been designed to provide such spacing and prevent damage to the intraocular lens during laser discissions. The pioneer lens in the field is that shown in U.S. Pat. No. Re. 31,626. This lens has a generally annular lip or ridge projecting rearwardly from the posterior surface of the lens, for contacting the posterior capsule and spacing the surface away from the lens. Another lens, shown in U.S. Pat. No. 4,412,359, has a rear lens surface that is concavely formed to space the central rear surface of the lens away from the posterior capsule. Still another lens, shown in U.S. Pat. No. 4,485,499, has a pair of support loops or risers formed separately from the lens, with each riser attached at its extremities to the posterior surface of the lens to space the lens from the posterior capsule.

The present invention is intended to enable another approach for spacing the rear surface of the lens from the posterior capsule which is particularly suited to low cost manufacture and reduced weight.

SUMMARY OF THE INVENTION

The present invention provides an intraocular lens for implantation in the posterior chamber of an eye, in a position spaced from the posterior capsule, to permit a laser discission to be performed without damaging the lens. The lens comprises a lens body and a pair of resilient lens centering strands or haptics emerging from the lens body. In accordance with the invention, the strands curve behind and underneath the lens body for contacting the posterior capsule and spacing it from the lens body, with the strands then curving outwardly and engaging eye tissue. This space provided by the strands advantageously prevents damage to the lens body when performing a discission with a laser. The intraocular lens of the present invention furthermore is intended to be simple in design, relatively inexpensive to manufacture, and reliable in use.

The lens body may be of varying shapes, and a lens body having a substantially planar rear surface, a convex front surface and a peripheral side edge may be used. The resilient lens centering strands each have a base end connected to the lens body and a curved free end for engaging eye tissue and centering the lens in the eye. Between its two ends, each strand curves in a generally spiral manner underneath and behind the lens to space the lens from the posterior capsule after implantation in the posterior chamber.

More particularly, the lens centering strand has a first portion connected to the lens body and projecting outwardly a short distance therefrom, and a second portion connected to the first portion that curves rearwardly and radially inwardly behind and underneath the rear surface of the lens in a substantially spiral manner. The strand further has a third portion connected to the second portion that curves radially outwardly from underneath the lens and flattens out into a straight leg portion extending a sufficient distance to engage eye tissue The first portion, second portion and third portion are integrally connected to form a continuous, homogenous strand. The strands preferably are located on diametrically opposed sides of the lens body and both curve in the same direction, that is, in either a clockwise or counterclockwise direction.

In a second embodiment of the lens, the first portion of the strand, when emerging from the lens body in a radially outward curvature, also curves forwardly of the lens body before joining the second portion, which curves rearwardly behind and underneath the rear surface of the lens in the manner described above.

The configuration of the lens strands advantageously spaces the rear surface of the lens from the posterior capsule after implantation of the lens following extracapsular cataract extraction. Thus, when performing a discission with a laser, the lens is spaced sufficiently outside the sphere of explosion created when the laser beam is properly focused on the posterior capsule and pulsed to open the clouded lens tissue. The spiral configuration of the strands in contact with the posterior capsule also provides a sufficient base to stabilize the lens against the posterior capsule, thus preventing possible tilting of an edge of the lens against the posterior capsule. A further significant advantage of the lens is that it has a simple design which is relatively inexpensive to manufacture. Thus, expensive lens molds and other costly manufacturing techniques, such as affixing risers or spacers to the rear face of the lens body, are avoided.

Other features and advantages of the present invention will become apparent from the following detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is a rear perspective view of a first embodiment of the invention, showing lens centering strands curving underneath and behind a lens body;

FIG. 2 is a bottom plan view of the lens of FIG. 1;

FIG. 3 is a cross-sectional view of the lens, taken substantially along line 3—3 of FIG. 2;

FIG. 4 is a side elevational view of the lens, taken substantially along line 4—4 of FIG. 2;

FIG. 5 is a cross-sectional view through a portion of a human eye, showing the lens implanted following extracapsular cataract extraction; and FIG. 6 is a cross-sectional view of a second embodiment of the lens, in which the strands curve forwardly before curving rearwardly behind and underneath the lens.

DETAILED DESCRIPTION OF THE PREFERRED EMBODIMENTS

As shown in the accompanying drawings, the present invention is embodied in an intraocular lens 10 for implantation in a human eye 12. In the preferred embodiment shown in FIGS. 1-4, the lens has a lens body 14 and a pair of strands 16 for centering the lens in the eye upon implantation after extracapsular cataract extraction. As described further below, the strands also function to space the lens from the eye's posterior capsule 18 and prevent damage to the lens body while performing a laser discission. The lens of this invention is intended to be simple in design, relatively inexpensive to manufacture, and reliable in use.

As shown best in FIGS. 3-4, the lens body 14 is plano-convex in diametric cross-section, having a substantially planar rear or posterior surface 20 and a convex forward or anterior surface 22. The peripheral configuration of the lens body is substantially circular, as defined by the continuous peripheral side edge 24 of the lens body, which is perpendicular to the rear planar surface of the lens. The optical corrective zone of the lens 10 is located in a central region 26 of the lens body. While the peripheral side edge of the lens body is shown as circular and the cross-section as plano-convex, any other desirable lens body configuration may be selected, and those shown are for purposes of illustration only.

The lens body 14 preferably is formed of transparent polymeric materials and the like suitable for lathe turning or molding by injection, compression or cast molding techniques. Materials suitable for this purpose include polymers such as polymethyl methacrylate, an example being that sold commercially under the trademark PERSPEX CQ.

The two lens centering strands or haptics 16 project from diametrically opposed edge portions 24 of the lens body 14. As described in conjunction with FIG. 5 below, the strands function to center and retain the lens 10 within the eye's posterior chamber 28 and to space the rear surface 20 of the lens body from the posterior capsule 18. The strands each have a base end 30 for connection to the lens body and a free end 32 for engaging eye tissue. The base end preferably is attached to the side edge 24 of the lens body so as to create as little interference as possible with the lens body. This may be accomplished by providing a bore 34 in the lens body by drilling or molding techniques, and inserting the base end of the strand into the bore. The inserted strand then may be permanently or removably secured within the bore by known adhesive, thermal or mechanical means. Alternatively, the strands and lens body may comprise a one-piece construction.

Material for constructing the strands 16 should have elastic properties so that the strands will return to a normal extended position after deformation, as best shown in FIG. 2. Thus, after deformation of the strands for implantation of the lens 10 in the eye 12 with an appropriate surgical instrument, the strands will be released by the instrument and tend to return to their normal extended position. Before the strands reach a fully extended position, however, they will engage eye tissue in the area of the ciliary sulcus 36 or capsular bag 38 (FIG. 5). Engagement with the eye tissue in this manner prevents the strands from fully extending and, therefore, the strands apply sufficient pressure to securely center and retain the lens within the eye. The strands preferably are formed of polypropylene, such as that sold commercially under the trademark PROLENE, or other suitable materials. The diameter of the strands may be on the order of 0.1 mm to 0.2 mm. If more than two strands are used, then a reduced strand diameter may be employed.

In accordance with the invention, the configuration of the strands 16 not only centers the lens 10 within the eye 12 as described above, but also advantageously provides a space 40 between the rear surface 20 of the lens body 14 and the posterior capsule 18, as best shown in FIG. 5. This space is especially useful when performing discissions or secondary posterior capsulotomies with a laser, because it provides a margin of safety by sufficiently spacing the lens body outside the sphere of explosion when the laser beam is properly focused on the clouded posterior capsule. This spacing prevents pitting and cracking of the lens body and other similar laser damage when the laser beam is pulsed to open the capsule.

More particularly, a first portion 41 at the base end 30 the strand 16 is connected to and extends radially outwardly a short distance from the peripheral edge 24 of the lens body 14 in a plane substantially parallel to the planar rear surface 20 of the lens body. The strand then includes a second portion 42 connected to the first portion that abruptly curves rearwardly and radially inwardly, in a substantially spiral manner, behind and underneath the rear surface. The strand curves in this fashion until it completes substantially a half circle and is at its most radially-inward point 43. At this most radially-inward point, however, the strands should not interfere with the optical corrective zone 26 of the lens body. Beyond this point 43, the second portion continues its circular curvature behind and underneath the rear surface, but now extending forwardly and radially outwardly until reaching the peripheral edge of the lens body. At this point, the strand gradually flattens out into a third substantially straight leg portion 44 extending away from the lens body and generally parallel to the planar rear surface. The strand terminates in the free end 32, preceded by a substantially curved or arched configuration of the third portion 44 for engaging eye tissue. The free end preferably is curved slightly back toward the lens body to prevent the strand end from pointing or jabbing against delicate eye tissue in the area where the lens 10 is implanted.

A significant feature of the strands 16 is their configuration behind and underneath the rear surface 20 of the lens body 14. This configuration is substantially spiral, thus providing a spring-like spacer between the rear surface and posterior capsule 18.

In a second preferred embodiment of the lens 10, as illustrated in FIG. 6, the first portion 41 of each strand 16 extends forwardly and radially outwardly a short distance from the peripheral edge 24 of the lens body 14, instead of extending in a plane substantially parallel to the planar rear surface 20 as in the first preferred embodiment (FIGS. 1-4). Thereafter the strand abruptly curves rearwardly and radially inwardly, in a substantially spiral configuration, behind and underneath the rear surface, as in the first embodiment. This second embodiment generally provides the same advantages as the first embodiment.

FIG. 5 illustrates the lens 10 of the present invention after it has been implanted in the human eye 12, in the posterior chamber 28 behind the eye's iris 46. The cataract has been extracted from the natural lens by extracapsular cataract extraction, leaving the intact posterior capsule 18 and an annular flap portion 48 of the extracted anterior capsule. The remaining portion of the natural lens capsule (i.e., the posterior capsule and annular flap portion) is connected to the ciliary muscle 50 of the eye through suspensory ligaments or zonules 52. It is noted that the posterior capsule prevents vitreous humor 54 located behind the posterior capsule from migrating forward.

The lens 10 may be implanted in the posterior chamber 28 through an incision in the periphery of the cornea 56 near the region of the angle 58 of the eye 12. The eye's pupil 60 preferably is dilated to facilitate access to the posterior chamber, with the free end 32 of one of the strands 16 inserted into the capsular bag 38 formed by the posterior capsule 18 and annular flaps 48, or, alternatively, in the region of the ciliary sulcus 36. The other strand may therafter be deformed and guided into place in the capsular bag or ciliary sulcus on a diametrically opposed side from the first-inserted strand. After implantation, the strands should be in a condition slightly compressed or deformed from their normal extended position to thereby maintain the lens body 14 in a correctly centered position within the posterior chamber. In this regard, the size of the lens body and length of the strands should be selected accordingly, in relation to the dimension of the patient's eye, to properly achieve the desired centering and fixation of the lens body.

Since the strands 16 curve behind and underneath the planar rear surface 20 of the lens body 14, upon implantation the strands will contact the posterior capsule 18 and create the space 40 between the posterior capsule and rear surface. This space advantageously positions the lens body outside the sphere of explosion created when the laser beam is pulsed to perform a discission or secondary capsulotomy of the posterior capsule. The precise amount of spacing between the rear surface of the lens body and the posterior capsule can vary, and a spacing of approximately 0.1 mm to 0.3 mm has been found sufficient to prevent damage to the lens body when the laser beam is properly focused on the posterior capsule. To achieve the desired spacing, the strand thickness and the coil diameter of the spring-like spacer portion of the strand can be selectively adjusted to create a sufficient spring-like force for urging the posterior capsule away from the rear surface. Thus, potential damage to the lens body by the laser explosion, typically in the form of lens pitting or cracking, is eliminated.

An additional advantage provided by the lens 10 of this invention is that the substantially spiral configuration of the strands 16 behind and underneath the lens body 14 provides a sufficient base area of contact with the posterior capsule 18 to securely stablize the lens against the posterior capsule. Thus, possible tilting of an edge 24 or rotation of the lens body against the posterior capsule is prevented.

Another significant advantage is that the lens 10 is simple and relatively inexpensive to manufacture. The lens comprises only the lens body 14 and the strands 16, and the formation and assemblage of these parts is relatively simple. Thus, expensive lens molds and complex lathe turning techniques are eliminated. Moreover, additional complicated and time consuming procedures to affix separate spacers or risers to the rear surface of the lens body are avoided.

While a particular form of the invention has been illustrated and described, it will be apparent that various modifications can be made without departing from the spirit and scope of the invention. Accordingly, the invention is limited only by the appended claims.

I claim:

1. An intraocular lens for implantation in the posterior chamber of the eye having a posterior capsule, comprising:
   a lens body having a front surface, a rear surface and a peripheral edge; and
   at least two strands connected to and projecting from said lens body for centering said lens body in the eye, each of said strands having,
   a first portion connected to the peripheral edge of said lens body and projecting radially outwardly therefrom, in a plane substantially parallel to the lens body's rear surface,
   a second portion connected to the first portion and curving rearwardly of the rear surface of said lens body to contact the posterior capsule and space the rear surface of said lens body therefrom, and
   a third portion connected to the second portion and extending radially outwardly relative to said lens body and terminating in a free end for engaging eye tissue.

2. The intraocular lens of claim 1, wherein said lens is adapted to be implanted in the posterior chamber of the eye after extracapsular cataract extraction leaving an intact posterior capsule, with said second portion of each strand adapted to contact the posterior capsule and sufficiently space the rear surface of said lens body from the posterior capsule to prevent damage to said lens body when performing a laser discission of the posterior capsule.

3. The intraocular lens of claim 2, wherein the space between the rear surface and the posterior capsule provided by said strands is approximately 0.1 mm to 0.4 mm.

4. The intraocular lens of claim 1, wherein the second portion of each strand curves in a substantially spiral manner behind and underneath the rear surface of said lens body in spaced parallel relation thereto to contact the posterior capsule and space the rear surface of said lens body therefrom.

5. The intraocular lens of claim 1, wherein the free end of the third portion of each strand has an arched configuration for engaging eye tissue without damage to such tissue.

6. The intraocular lens of claim 1, wherein the first portion, second portion and third portion of each strand are integrally connected to form a continuous, homogenous strand.

7. The intraocular lens of claim 1, wherein said strands are positioned on diametrically opposed portions of the peripheral edge of said lens body.

8. The intraocular lens of claim 1, wherein the rear surface of said lens body is substantially planar and the front surface of said lens body is substantially convex.

9. An intraocular lens for implantation in the posterior chamber of the eye after extracapsular cataract extraction leaving an intact posterior capsule, comprising:
   a lens body having a front surface, a rear surface and a peripheral edge; and
   a plurality of strands connected to and projecting outwardly from said lens body for centering said lens body in the eye, each of said strands having
   a first portion connected to the peripheral edge of said lens body and projecting radially outwardly therefrom in a plane substantially parallel to the rear surface,
   a second portion connected to the first portion and curving rearwardly and radially inwardly behind and underneath the rear surface of said lens body in a substantially spiral manner, and
   a third portion connected to the second portion and extending radially outwardly relative to said lens body and terminating in a free end having a substantially arched configuration for engaging eye tissue without damage to such tissue,
   whereby a segment of each of said strands is adopted to contact the posterior capsule of the eye and sufficiently space the rear surface of said lens body from the posterior capsule to prevent damage to said lens body when performing a laser discission of the posterior capsule.

10. The intraocular lens of claim 9, wherein the space between the rear surface and the posterior capsule provided by said strands is approximately 0.1 mm to 0.4 mm.

11. The intraocular lens of claim 9, wherein said plurality of strands comprises two strands positioned on diametrically opposed portions of the peripheral edge of said 12. The intraocular lens of claim 9, wherein the rear surface of said lens body is substantially planar and the front surface of said lens body is substantially convex.

13. An intraocular lens for implantation in the posterior chamber of the eye after extracapsular cataract extraction leaving an intact posterior capsule, comprising:
   a lens body having a front surface, a rear surface and a peripheral edge; and
   a plurality of strands connected to and projecting outwardly from said lens body for centering said lens body in the eye, each of said strands having
   a first portion connected to the peripheral edge of said lens body and projecting forwardly of and radially outwardly therefrom,
   a second portion connected to the first portion and curving rearwardly and radially inwardly behind and underneath the rear surface of said lens body in a substantially spiral manner, and
   a third portion connected to the second portion and extending radially outwardly relative to said lens body and terminating in a free end having a substantially arched configuration for engaging eye tissue without damage to such tissue,
   whereby a segment of each of said strands is adopted to contact the posterior capsule of the eye and sufficiently space the rear surface of said lens body from the posterior capsule to prevent damage to said lens body when performing a laser discission of the posterior capsule.

14. The intraocular lens of claim 13, wherein the space between the rear surface and the posterior capsule provided by said strands is approximately 0.1 mm to 0.4 mm.

15. The intraocular lens of claim 13, wherein said plurality of strands comprises two strands positioned on diametrically opposed peripheral edges of said lens body.

16. The intraocular lens of claim 13, wherein the rear surface of said lens body is substantially planar and the front surface of said lens body is substantially convex.

* * * * *